United States Patent [19]

Olson et al.

[11] 4,127,648

[45] Nov. 28, 1978

[54] ICHORIN AND ITS USES

[76] Inventors: George B. Olson, University of Arizona, Bldg. 90, Tucson, Ariz. 85721; Clairmont Drube, 40 Conger St., Bloomfield, N.J. 07003

[21] Appl. No.: 813,584

[22] Filed: Jul. 7, 1977

[51] Int. Cl.$^2$ ............ A61K 39/40; A61K 39/42; A61K 35/16
[52] U.S. Cl. .................... 424/86; 424/85; 424/87; 424/101
[58] Field of Search ............ 424/85, 86, 87, 101

[56] References Cited

U.S. PATENT DOCUMENTS

| 2,516,206 | 7/1950 | Harms | 424/87 |
| 3,664,994 | 5/1972 | Perper | 424/85 |
| 3,719,182 | 3/1973 | Rose | 424/85 |

*Primary Examiner*—Sam Rosen
*Attorney, Agent, or Firm*—Merriam, Marshall & Bicknell

[57] ABSTRACT

This application relates to novel blood serum fractions, Ichorin, Ichorin$_1$ and Ichorin$_2$, capable of transferring cell mediated immunity, and to the methods for the preparation and use thereof.

30 Claims, No Drawings

ICHORIN AND ITS USES

This invention relates to Ichorin, and to the methods for the preparation and use thereof. More specifically, this invention relates to the novel substance Ichorin, a biologically active substance capable of passively transferring immunological information from one animal to another, and to the methods for the preparation and use of Ichorin. Still more specifically, this invention relates to Ichorin, a novel blood-serum fraction isolate capable of transferring cell-mediated immunity from one animal to another, to the electrophoretic procedures for the isolation of said fraction, and to the use of the isolated fraction, with or without further purification, either alone or in conjunction with other chemotherapeutic agents, in the treatment and/or prevention of disease states.

Over the past several years much has appeared in the literature concerning biologicals obtained from lymphoid tissues which have been reported to have passively transferred delayed type sensitivities and which have been reported to impart immunological protection in certain chronic disease states. These biologicals, for lack of a better term, have been termed "transfer factors" and are alleged to have beneficial effects against bacterial, viral, fungal and parasitic infestations, and neoplasisa.

Indeed, in recent years some of these "transfer factors" have been used in the treatment of certain disease states in immunological deficient patients who are chronically infected with various types of microbial agents. Unfortunately, response to such therapy has been too variable — perhaps due to the source and/or to the techniques for the obtainment of the "transfer factors" and therefore clinical application has been somewhat limited. Coincidental with the development of the thesis relating to the "transfer factors" concept, we have discovered that a certain isolate obtained from blood serum is capable of passively transferring delayed-type sensitivities, and is also capable of being utilized as a chemotheropeutic agent to protect animals against viral and fungal diseases. Further, the isolates have the ability to lower the effective dosage amounts of known chemotherapeutic agents in the treatment of viral and fungal diseases. This isolate of blood-serum has been termed "Ichorin."

Ichorin is a substance which is essentially comprised of components which uniformly and consistently appear when produced according to the methods described herein. It is released by physical-chemical means from the sera of warm blooded animals and may be characterized in that it

- is capable of passively transferring immunological protection to naive subjects,
- is a substance which can passively transfer immunological competency across animal species barriers,
- is a substance which can be obtained from sera of actively sensitized subjects or from sera of subjects of unknown immunological competence,
- is a substance which possesses an electrophoretic range equivalent to the range demonstrated by alpha globulins, albumins and pre-albumins and which can be fractionated by Amicon filtration to a molecular weight range of 500-10,000 daltons,
- is a substance which, in part, depicts visible components having molecular weights of 1,500 to 5,000 daltons (as demonstrated by thin layer chromatography),
- is a substance which can be lyophilized to a white powder and which is easily reconstituted in water,
- is a substance which, when dissolved in saline at an acid pH of 3.8, has an optical density ratio of 280/260 in the range of 0.20 to 0.58,
- is a substance which can be further subdivided into individual components by polyacrylamide gel electrophoresis,
- is a substance which can be further subdivided into individual components by thin layer chromatographic procedures,
- is a substance which will passively transfer delayed type hypersensitives to a naive animal as evidenced by typical skin test reactions and by mononuclear cell infiltration into the surrounding tissues,
- is a substance which will instruct lymphocytes obtained from naive animals to produce a lymphocyte mediator termed "lymphocytes blastogenic factor" when cultured in vitro with the specific antigen,
- is a substance which will instruct lymphocytes obtained from naive animals to produce a lymphocyte mediator termed "macrophage migration inhibition factor" when cultured in vitro with the specific antigen,
- is a substance which will affect the lymphocytoporesis of lymphocytes located in the thymus dependent areas of lymphoid tissues,
- is a substance which when administered to animals prior to, simultaneously with, or after induction of a viral or fungal disease will impact immunological protection to the animals.

Additionally, in terms of its physical and chemical characterization, Ichorin is not orcinol positive and it does take a Ninhydrin stain. When subjected to analysis via a silica gel plate using a chloroform/methanol/ammonia (2/2/1) system it has two ultraviolet absorption spots which move on the plate.

The preparation of Ichorin begins with the preparation of suitable antigens which are injected into animals so as to sensitize the animal. Following sensitization the animals are bled and, after suitable clotting time, the serum is removed and lyophilized for storage until subjected to the electrophoresis procedures utilized to isolate Ichorin. The antigen preparation, animal sensitization, serum isolation and lyophilization are all done according to procedures which are well known in the art.

In general, the isolation of Ichorin may be described as a block electrophoresis of blood serum under certain pH and ionic conditions to produce an alpha-gamma globulin complex, which complex is dissociated and isolated by an additional electrophoretic procedure. More specifically, Ichorin is obtained by subjecting blood serum or plasma of an animal to a series of at least two electrophoretic procedures, said electrophoresis being conducted on a Geon-Pevikon Block according to the techniques described by Fahey in J. Immunology, 91, 1963, pg. 484. Essentially, the first electrophoretic separation utilizes a 0.05 ionic strength, pH 8.2 Veronal buffer (sodium barbital-sodium acetate) with a constant current of 50 milliamps and about 300 volts for about 18 hours at 6° C. The serum is applied 14 cm from the cathode end of block. The proteins are removed from the Geon-Pevikon strips via water elutions and, utilizing $OD_{280}$ and immunoelectrophoresis readings, separate pools of gamma, beta and alpha globulins and albumin are isolated. The gamma globulin pool (coded as Block I-γ material), is further treated whilst the beta and alpha globulin pools are lyophilized and stored for other uses.

The Block I-γ globulin pool is desalted (via filtration through an Amicon UMO-5 filter) and the desalted retentate is subjected to a second electrophoretic procedure utilizing a 0.025 ionic strength, pH 8.2 Veronal buffer with a constant current of 10–20 milliamps and about 400–500 volts, preferably 450 volts, for about 18 hours. The material is applied 14 cm from cathode end of block. Of course normal variations to these precise conditions will achieve the same results, but less efficiently. The proteins are again eluted and, again utilizing optical $OD_{280}$ and immunoelectrophoretic readings, a gamma globulin pool and a second pool with an electrophoretic mobility in the alpha region are obtained. Each pool is desalted and the gamma globulin pool is coded as Block IIγ whilst the other pool is called Ichorin. The Ichorin-containing segments are the 15–32 centimeter sections. If desired the separation into two of its component parts (ie. $Ichorin_1$ and $Ichorin_2$) from the so-produced Ichorin may be effected by column chromatographic techniques utilizing a chloroform/methanol/ammonia (2:2:1) developing system from Silica gel.

Alternatively, Ichorin may be separated from an amonic ionic exchange column, eg. a diethylaminoethyl (DEAE) cellulose by adding a desalted Block Iγ region to the column, eluting off the alpha and beta globulins and the serum proteins utilizing a decreased ionic strength double distilled water solvent (0.01) and then removing the Ichorin with an increased ionic strength double distilled water.

Having described in general terms the procedures useful for the ultimate obtainment of Ichorin, the following specific examples will more explicitly illustrate the techniques, methods and materials suitable for carrying out this invention.

Preparation of Antigens

Preparation of Candida antigens:

Preparation of Candida heat killed antigens (soluble and whole cell antigens). *Candida albicans* (Wisconsin) is grown in a New Brunswick 4.5 liter fermentor. Chemically defined medium containing 5g $NH_4CL$, 1g $NH_4NO_3$, 2g $NO_2SO_4$, 3g $K_2PO_4$, 1g $KH_2PO_4$, 0.1g $MgSO_4.7H_2O$, 40g Dextrose and 50 mg of Biotin per liter of distilled water is used. The culture is grown at 30° C for 72 hours with constant stirring (200 rpm) and aeration (3 liter per minute). The culture is terminated by heating at 70° C for 6 hours and the broth is cleared by centrifugation and filtration through a 0.45 Millipore membrane filter. The whole cells are sonicated and thoroughly washed with methanol and acetone. The cellular antigen is resuspended in a small volume of distilled water. The cleared broth is then lyophilized to dryness, reconstituted in a small volume of distilled water and dialyzed at 4° C against 10 changes of 10 volumes of distilled water. The soluble and whole cell Candida antigens are lyophilized to dryness. Both are stored at 4° C.

Preparation of Listeria antigens:

Preparation of Listeria formalinized antigen. *Listeria monocytogenes* IS0-30556 is grown in a 4.5 liter New Brunswick fermentor. Difco tryptose phosphate broth is used. The culture broth is inoculated with a ten ml 18 hour TPB starter and then incubated for 48 hours at 37° C with stirring (200 rpm) and aeration (3 liter per minute). The culture is terminated by formalizing with a final concentration of 1% formalin, left stationary for 24 hours at room temperature, and then centrifuged. The killed organisms are collected and washed 5 times with saline and finally two times with distilled water. After the final wash, the killed organisms are suspended in a small volume of distilled water, sonicated, lyophilized to dryness, and stored at 4° C.

Preparation of Serum

Guinea pigs of approximate 700 g body weight are injected simultaneously with about 5 mgm of killed candida antigenic material previously suspended in Freund's complete or incomplete adjuvant. Approximately three weeks following injection (sensitization) the animals are bled to obtain maximum amounts of blood. Allow the blood to clot for 1 hour at 37° C, then removed and allowed to clot for an additional six hours at 4° C. The serum is removed and lyophilized.

Similarly, guinea pigs are sensitized with Listeria antigen and by following the same procedure set forth for the obtention of the serum of Candida sensitized animals there is obtained serum having Listeria sensitized factors. Of course, if it is desired to obtain Ichorin useful for treating other disease states, the appropriate antigen is prepared, the animals sensitized and the serum isolated according to the foregoing techniques, said techniques being well known to those of ordinary skill in the art.

Electrophoretic Separation of Serum

Block I Procedure

The following reagents, equipment and procedures are utilized for the separation of Ichorin from the serum.

Reagents:

(1) 240 g. Geon (2) 240 g. Pevikon (3) Barbital buffer, pH 8.2, 0.05 ionic strength (sodium barbital, 0.03M, sodium acetate, 0.02M and acetic acid 0.01M)

(4) 12 Grams of lyophilized serum reconstituted in 15 ml double distilled water. (NB Bromphenol blue may be added to serve as an electrophoretic marker).

Equipment:

(1) Coarse filter mounted on vacuum flask. (To wash away fine particles found in the Geon and Pevikon materials).

(2) 24 × 37 cm, plexiglass tray. (To serve as the electrophoresis tray).

(3) Telfa wicks. (To act as connectors between the buffer chambers and the electrophoresis tray).

(4) Parafilm. (To line the electrophoresis tray and surround the Geon-Pevikon material).

(5) Towels. (For removing excess buffer from electrophoresis block).

(6) Saran Wrap. (To cover Geon-Pevikon block during electrophoresis).

(7) Buffer chambers with baffles and electrodes.

(8) Direct current power source.

(9) Filter with Whatman No. 1 or appropriate type filter paper.

(10) Syringe and 20 g. needle or equivalent instrument to apply sample to Geon-Pevikon block.

Procedure:

(1) Geon and Pevikon powders are combined in a large beaker and stirred to a slurry in 600 ml. distilled water. (Some commercial preparations of Geon and Pevikon require an additional procedure to assure good wetting of the particles. This may be accomplished by placing the slurry into a vacuum flash and creating a negative pressure for 15 minutes or more. Slurry may also be treated with 25-50 ml. absolute methyl alcohol to increase wetting of the particles).

(2) Slurry is poured into coarse filter allowed to set, the fines are removed and the remaining water is removed by suction.

(3) 600 ml. water is added to coarse filter and particle mixture stirred to slurry allowed to settle, fines are removed and again suctionized to remove excess water.

(4) Operation No. 3 is repeated two times.

(5) After the last water wash, the mixture is sucked dry.

(6) 600 ml. Barbital buffer added to coarse filter, and particles again stirred to slurry and sucked dry.

(7) Dried mixture is removed to a beaker, and filter is rinsed free of particles with 300 cc Barbital buffer which is added to the beaker.

(8) Plexiglass tray is lined with Parafilm which extends up the sides of the tray and about ½ inches above.

(9) Telfa wicks are placed across each end of the tray and their ends laid on clean towels.

(10) Slurry is poured evenly into plexiglass tray.

(11) Excess buffer is allowed to drain thru wicks onto towels for about 20 minutes.

(12) A slot is then cut across the block with a small spatula guided by a ruler about 14 cm. from the cathode end. Slot should end 1 cm. from each wall and should extend almost, but not quite, to the bottom of the block.

(13) Sample (15mls) with bromphenol blue is delivered evenly along total length of slot with syringe and a 20 gm. needle. The slot is closed after equilibration by packing the sides together with a small spatula.

(14) Block is then allowed to equilibrate in for 15 minutes.

(15) Block is placed above and between two 15 × 16 × 30 cm. buffer chambers and the wicks allowed to drop into the buffer chambers.

(16) Each buffer chamber contains 3baffles. The one furtherest from the block is strung with the platinum electrode.

(17) Each buffer chamber contains about 4 L of barbital buffer which has been cooled to 3° C.

(18) Block is covered with Saran Wrap.

(19) A constant current of 50 ma and about 300 v is applied for approximately 18 hours.

(20) A "Danger, High Voltage" sign is erected in front of the apparatus.

(21) After electrophoresis, the block is removed from buffer chambers.

(22) Excess buffer is allowed to drain through the wicks onto towels for about 10 minutes.

(23) Bands of protein may be located by placing the block above a small X-ray viewing box and observing position of bromphenol blue and any other color associated with various serum proteins.

(24) The entire electrophoresis block is cut in strips of 1 cm. width with a small spatula.

(25) Each 1 cm. width section is suspended in distilled water and placed in a filter with Whitman No. 1 filter paper. Eluted protein is removed by suction.

(26) Each section is suspended three times in 7 ml. volumes of double distilled water and suctioned into a small Erlenmeyer flask with a side arm.

(27) Eluates are centrifuged to remove polyvinyl particles if necessary.

(28) Eluates are generally analyzed by OD 280 immunoelectrophoresis to ascertain to purity of each 1 cm. width section. Sections containing similar materials are pooled and analyzed further.

Block II Procedure

Reagents:
(1) 240g Geon
(2) 240g Pevikon
(3) Barbitol Buffer, pH 8.2, 0.025 ionic strength (4.8 liters of Barbitol Buffer Block I procedure, step 3 in 7.2 liters distilled $H_2O$).
(4) Sample, 1g lyophilized material (Block I gamma globulin) reconstituted in double distilled water to 10 ml total volume.

Equipment:
Same equipment

Procedure:
Same as for the Block I procedure except step 21 wherein a constant current of 10 (and up to 20) milliamps and about 400 (and up to 450) volts is applied for approximately 18 hours.

(1) The pooled elutes from the α region of block II containing Ichorin (15-32 cm sections) are lyophilized to dryness and resuspended in 100 mls of double distilled water.

(2) The aqueous solution of Ichorin is placed on an Amicon P-10 Amicon Ultrafiltration membrane in a model 202 filter.

(3) The P-10 cell filtrate tube is connected to a second Amicon 202 cell equipped with an UMO5 Ultra filter membrane.

(4) Attach to P-10 cell a source of nitrogen gas at 55 lbs psi. Push the contents of P-10 cell into the UMO5 membrane equipped cell. Leave about 20 mls in the P-10 cell and start passing double distilled water through the P-10 filter into the UMO5 equipped chamber. This is done by employing a reservoir equipped with proper monifold.

(5) Pass 500 mls of double distilled $H_2O$ through the P-10 into the UMO5 filter. The UMO5 filter chamber will be about 4/5th full. Shut off the flow of water and pass nitrogen gas through until all water is clear from supply tubes. Shut off all supply of nitrogen pressure. Release pressure first from the UMO5 cell and then the pressure from the P-10 cell.

(6) Disconnect the supply tube to the P-10 cell and the drain tube of P-10 cell to the UMO5 cell connect the source of nitrogen gas to the UMO5 cell and rum at 55 lbs psi until volume is reduced to 20 mls. Now pass 200 mls of double distilled $H_2O$ through this cell.

(7) Disconnect the cells and lyophilize to dryness the retentates of the P-10 and UMO5 cells. Store under vacuum at 4° C.

(8) The P-10 cell contains the material greater than 10,000 molecular wt and the retentate of the UMO5 cell contains the Ichorin (mol. wt. between 500–10,000). The filtrate contains material less than 500 mol. wt. Discard the filtrate.

Immunoelectrophoretic analysis of samples obtained from Geon Pevikon Block Electrophoresis Material:
1. Agarose (Sigma No. 6877) suspended to a 0.8% concentration in appropriate buffer.
2. Sodium barbital buffer. pH 8.2 and ionic strength 0.05. Sodium barbital 0.03M, Sodium acetate, 0.02M and acetic acid 0.01M).

3. Glass plates 4¼ × 3¼ size to hold the agarose.
4. DC power source.
5. Electrophoretic cell holder for glass plates.
6. Wicks to connect the agarose plates to the buffer chambers of the electrophoretic cell holder.

Procedure:

1. Agarose at a concentration of 0.8% is suspended in buffer and heated to make a homogenous gel. Gel is applied to glass plate to a thickness of 2-3mm, allowed to harden. (15 mls)

2. A series of wells is punched into the gel at a distance of 4cm from one of the ends of the plate. The gel is removed from each well.

3. Plate is placed on the electrophoretic chamber and the wicks are applied. Samples to be analyzed and appropriate controls are placed individually into the series of open wells. Each well will contain approximately 10 lamba of material.

4. A constant current of 2.5 ma per cm is applied for approximately 1 hour. All proteins are separated in the electrophoretic field with albumin moving farthest towards the anode, followed by $\alpha, \beta$ and $\gamma$-globulins, respectively.

5. Plate is removed from the electrophoretic chamber, wicks removed and a trough is cut in the gel between each of the wells. (Troughs are cut to run from anode to cathode ends of the plate).

6. Antiserum with specificity directed against the samples is added to each trough. Plates are incubated at room temperature in a humid atmosphere.

7. Within 4-48 hours (depending upon the strength of the reacting substances) precipition bands of antigen (samples) and homologous antibodies are formed.

8. Each sample is checked to ascertain the number type of components present (Note How?).

9. Samples containing similar materials are identified. Consequently, the original 1 cm width sections from Geon Pevikon electrophoretic blocks can be pooled and subjected to further analysis.

10. In general, analysis of 1 cm width sections from Geon Pevikon shows the following:

cm widths 8-14 contain gamma globulins.
cm widths 15-17 contain beta globulins.
cm widths 18-22 contain alpha globulins.
cm widths 23-30 contain albumins.
cm widths 31-34 contain pre-albumins.

Isolation of Ichorin with diethylaminoethyl (DEAE), cellulose anionic-ionic exchange chromatography from Block I $\gamma$ region may be utilized as an alternate method from the Geon-Pevikon Block II electrophoretic process. The method employs DEAE cellulose (as an anion exchanger) to absorb proteins other than gamma globulin from an antiserum (See E. A. Peterson, H. A. Sober, Chromatography of Proteins I. Cellulose Ion-Exchange Absorbents, J. Am. Chem. for 78, 715 (1956) the Peterson et al Method of using a column of DEAE cellulose to absorb non-gamma globulin components whole serum, and subsequently eluting these components as various fractions achieved the intended fractionation. However, a less complicated procedure of Stanworth (See D. R. Stanworth, A Rapid Method of Preparing Pure Serum Gamma Globulin, Nature, 188, 156 (1960) is adequate for obtaining a separation of Ichorin from gamma-Ichorin complex obtained from Block I $\gamma$ region. The following procedure will separate the Ichorin from Gamma-Ichorin complex of 45 mls of serum.

Part A:

1. Lyophilized Block I $\gamma$ region of three Geon-Pevikon Block I preparations of whole serum (15 mls whole serum per block) suspended in 25 ml double distilled water is placed on an UMO-5 Amicon filter membrane in a Model 202 Amicon high pressure cell. Pass 500 mls of double distilled water over the retentate with 55 psi of nitrogen (This preparation to be used in Step 4 in Part B).

Part B: (Separation of gamma globulin from Ichorin) (NB. all steps performed at 8°–10° C)

1. Prepare an aqueous slurry of about 45g of dry, clean DEAE cellulose, equivalent to 340 to 350 g of wet regenerated material (see step 6, part C below), and pour the slurry into a medium fritted glass funnel or Buchner funnel previously fitted with filter paper.
2. Remove as much water as possible from cellulose by suction.
3. Add in 100 ml aliquots about 500 ml of sodium phosphate-saline buffer (0.01M phosphate, 0.015M NaCl, pH 7.5).
4. Allow the last dilution of buffer to filter through the cellulose by gravity in order that the right degree of moisture results. Remove the cellulose from the funnel for weighing.
5. Weigh 340g of the wetted DEAE cellulose into a 600-ml beaker: Add 50 ml of the 0.01M phosphate buffered saline, and mix.
6. Slowly add the prepared Block I $\gamma$-region with continuous stirring to the suspension of cellulose.
7. Allow the solution to stand for 5 hours.
8. After the equilibration with Block I $\gamma$-region in step 5 add 100 mls of buffer saline (0.01M) with stirring.
9. Filter the suspension under suction, add 5 aliquots of 100 mls of buffered saline (0.01M) with stirring and filtration under suction. The filtrate will contain gamma globulin test samples with immunoelectrophoresis.

Part C: Release of Ichorin from DEAE (All steps performed at 8° to 10° C)

1. Cellulose material from step 7 part B contain Ichorin add 100 mls of 0.3 phosphate buffered saline with constant stirring. Let stand for 5 hours.
2. After equilibration with phosphate buffered saline (0.5M), add 100 mls of buffer with stirring.
3. Filter suspension under suction, rinse with 5 aliquots of 100 mls of buffer. Lyophilize filtrate to dryness.
4. Resuspend lyophilized material from step 3 in 25 mls of double distilled water.
5. Pass suspension from step 4 through a P-10 Amicon ultifilter (Model 202) to remove and material with molecular weight greater than 10,000. Continue the filtration through a UMO-5 amicon ultra filter to retain any material greater than 500 molecular weight. The retentate on the UMD5 filter is lyophilized to dryness. This is the Ichorin preparation.
6. Regenerate the DEAE cellulose for reuse by the following procedure:
   a. Wash the cellulose several times with large volumes of distilled water, with suction remove the water. Follow with an initial wash with 0.1N NaOH, then by distilled water.
   b. Continue treatment under suction while alternating acid and base with distilled water washing in 200-300 ml amounts, i.e., 0.1NHCl, then distilled $H_2O$, 0.1N NaOH, then distilled $H_2O$. Repeat cycle three or four times.
   c. The cycle should end with base, followed by washing several times with distilled water.

d. Store as an aqueous suspension or, if the cellulose is to be used immediately, continue washing with buffer (step 1, part B).

Other materials which will create a change in the ionic condition responsible for containing the Ichorin in the Block I-γ complex are; Amicon Ultra filtration, dialysis, affinity chromatography and preparative electrophoresis procedures. These all are alternate methods of preparing Ichorin from hyperimmune and "normal" sera.

Separation of $Ichorin_1$ and $Ichorin_2$ from Ichorin

Pack a column (3.5 cm in diameter to a height of 53 cm) by allowing a thoroughly solvent-washed slurry of silica gel (60–200 mesh) to settle by gravity. Rewash the bed with 10 volumes of solvent (a 2/2/1 mixture of chloroform/methanol/ammonia (conc. $NH_4OH$).

Lyophilize a water slurry containing 1.9 g of Ichorin (from the Block II electrophoretic process) and 1.9 g of silica gel. Dust the lyophilized material onto the top of the column and slowly add solvent to the column. Adjust the flow rate of solvent (chloroform/methanol/ammonia-2/2/1) to 1 ml per 5 minutes.

Samples are analyzed by spotting 20 lamba of every fifth sample on a Silica Gel GF (Analtech), 250 microns thick thin layer chromatograph plate. The plates are developed in chloroform/methanol/ammonia (2:2:1) solvent and $Ichorin_1$ and $Ichorin_2$ are observed by the samples having short wave (254 nm) U.V. absorbance with Rf values of 0.84 and 0.66 respectively. Samples are pooled and evaporated to dryness with a Buchi rotovaparator. The material is brought up in double distilled water and lyophilized to dryness to yield 726 mgm of $Ichorin_1$ and 350 mgm of $Ichorin_2$.

In preliminary studies comparing Ichorin and "transfer factor" preparations, it was demonstrated that both products possess similar biological properties in that both can passively transfer specific cutaneous hypersensitivity in vivo, both can recruit normal lymphocytes in vitro to give positive reactions in the migration inhibition factor test and lymphocyte stimulation test, and both are effective in crossing species barriers to protect mice against lethal infections of *Candida albicans*. Thus, these studies show that Ichorin, obtained from hyperimmune sera, can serve as a therapeutic agent in treatment of chronic disease states, and that it may also be used for the reconstitution of a "normal" immune response in immunologically depressed systems.

Further studies on isolated preparations of Ichorin and "transfer factor" from guinea pigs and sheep, as well as Ichorin indicate that both "transfer factor" and Ichorin transfer delayed type hypersensitivity between animal species. In these studies, the preparations are evaluated by skin testing in guinea pigs for the ability to transfer delayed type hypersensitivity to the specific allergens with which the donor animals have been sensitized. The preparations displayed the appropriate immunological specificity. For example "Candida Ichorin" transferred type hypersensitivity to Candida antigen but not to Klebsiella, while "Klebsiella Ichorin" transferred delayed type hypersensitivity to Klebsiella but not Candida antigen, etc.

Investigations have also been conducted on the therapeutic use of these agents in in vivo protection studies of mice infected with Candida and influenza virus. FIG. 1 shows the effect of Candida Ichorin and transfer factor on the survival of mice given a lethal Candida infection. The mice were administered a single intraperitoneal dose if Ichorin or transfer factor (3, 6, or 9 mg/kg bodyweight) at different times (−3, 0 or +3 days). Although there does not appear to be a simple dose-response relationship, both agents at all three dosages led to significant survival over that observed in control animals, particularly when given prophylactically (3 days before infection).

TABLE I

Effect of Guinea Pig Ichorin and Transfer Factor Treatment on the Survival of Candida albicans-infected* Mice

| | Percent Survival*** | | | | | |
|---|---|---|---|---|---|---|
| | Ichorin (mg/kg, i.p.) | | | Transfer Factor (mg/kg, i.p.) | | |
| Day of Treatment** | 3 | 6 | 9 | 3 | 6 | 9 |
| −3 | 20 | 50 | 60 | 60 | 90 | 40 |
| 0 | 40 | 20 | 40 | 90 | 70 | 50 |
| +3 | 20 | 20 | 20 | 60 | 40 | 40 |

*CFl mice, male, 20 grams each, injected i.v., with 810,000 Candida albicans (Wisc.) organisms in a caudal vein.
**day of treatment relative to administration of Candida.
***Percent survival thirteen days post infection (all untreated control animals dead). Ten animals per group.

The possibility that concomitant treatment with some antiinfective agent might lead to further increased survival, prompted a parallel study on the effects of combined therapy with cell mediated immunity factors plus the antifungal, Amphotericin B. Some results of this investigation are presented in Table II. Mice treated as before with Ichorin or transfer factor and infected with a lethal dose of Candida, were given a single subtherapeutic dose (3 mg/kg bodyweight, s.c.) of Amphotericin B. (This amount is one-tenth the usual total protective dose of 6mg/kg daily for 5 days). As can be seen, the combination therapy resulted in significant survival compared to that observed in control animals receiving no treatment, cell mediated immunity factors alone or Amphotericin B. alone.

TABLE II

Effect of Combined Amphotericin B* plus Ichorin or Transfer Factor Therapy on the Survival of Candida albicans-infected** Mice

| | Percent Survival**** | | | | | |
|---|---|---|---|---|---|---|
| | Ichorin (mg/kg, i.p.) | | | Transfer Factor (mg/kg, i.p.) | | |
| Day of Treatment*** | 3 | 6 | 9 | 3 | 6 | 9 |
| −3 | 100 | 90 | 90 | 70 | 100 | 60 |
| 0 | 90 | 90 | 90 | 70 | 80 | 70 |
| +3 | 70 | 70 | 100 | 90 | 90 | 80 |

*Amphotericin B (Fungizone), 3 mg/kg, s.c. on day 0.
**810,000 Candida albicans (Wisc.) organisms, i.v. per animal.
***day of treatment relative to administration of Candida.
****Percent survival 30 days post-infection. Ten animals per group. Non-treated control mice were all dead by day 13.

We have also examined the effect of guinea pig Ichorin and transfer factor on viral infections in mice. Mice given an intranasal $LD_{50}$ dose of influenza virus were treated −3, 0, or +3 days post infection with either 2 or 5 mg/kg bodyweight of influenza specific Ichorin or transfer factor. Some of the results are presented in Table III.

TABLE III

Effect of Guinea Pig Ichorin and Transfer Factor on the Survival of Influenza Virus-infected Mice

| | Percent Survival** | | | |
|---|---|---|---|---|
| | Ichorin (mg/kg, i.p.) | | Transfer Factor (mg/kg, i.p.) | |
| Day of Treatment* | 2 | 5 | 2 | 5 |
| −3 | 50 | 90 | 100 | 90 |
| 0 | 50 | 30 | 50 | 60 |

TABLE III-continued Effect of Guinea Pig Ichorin and Transfer Factor on the Survival of Influenza Virus-infected Mice

| Day of Treatment* | Percent Survival** | | | |
|---|---|---|---|---|
| | Ichorin (mg/kg, i.p.) | | Transfer Factor (mg/kg, i.p.) | |
| | 2 | 5 | 2 | 5 |
| +3 | 70 | 50 | 70 | 40 |

*day of treatment relative to administration of Candida.
**Percent survival 15 days post-infection with 1 $LD_{50}$ of influenza virus ($A_2Jap$ 305-57) given intranasally. Ten animals per group.

As will be obvious to one of ordinary skill in the art the techniques for using and the uses for Ichorin will parallel the use of the known transfer factors. This notwithstanding, a few comments may be in order concerning the non-specific and specific Ichorin. (Specific Ichorin is that Ichorin which is derived from the blood serum of an animal which has been specifically sensitized to a specific bacterial, fungal, viral or parasitic antigen.)

In general, non-specific Ichorin may be used to treat those warm-blooded animals which are immunologically incompetent, i.e. those animals which are immune deficient (either genetically or traumatically) in that they fail to react to foreign materials such as bacterial, fungal, viral or parasitic antigens. More specifically, it is suggested that the non-specific Ichorin may be used in situations such as treating military personnel when such personnel are entering geographical areas containing a high incidence of diseases to which the military personnel may not have been previously exposed. Another is the treatment of burn patients, surgical transplant patients (particularly those receiving immunosuppressants) and in certain instances in treating immune deficients suffering from leprosy, tuberculosis, and the like, including cystic fibrosis.

Still another use for the non-specific Ichorin (derived from bleeding a "normal" individual or by using pools from outdated blood-bank serum or plasma) is used in the treatment of rheumatoid arthritis and ataxia-telangiectasia. Further, Ichorin may be derived from "normal" individuals who may be termed "coinhabitants" or those normals to have natural immune effects; such Ichorin being useful in the treatment and surveilance of tumors (Melanoma, Osteogenic sarcoma; Rhabomyosarcoma, Leomyosarcoma, Wilms tumor, Renal Cell Carcinoma, Epidermal Carcinoma, Adenocarcinoma, Lymphosarcoma, Neuroblastoma, Fibrosarcoma, Acute Lymphocylic Leukemia, Basal Cell Carcinoma, Multiple Myeloma, Synovial Sarcoma) the Wiskott-Aldrich syndrome, subacute Sclerosing panencephalitis, Multiple sclerosis, and may also be used to re-constitute full immunological states of warm-blooded animals who have been treated with immunosuppressants. Similarly, acute bacteremia and septicemia may be treated with Ichorin particularly wherein the present chemotherapeutic agents have a low therapeutic index. Organisms which have a high degree of resistance and would be particularly susceptible to this type of treatment are: Staphococcus, Pseudomonas, Klebsiella Streptococcus, Proteus, Serratia, *Escherichia coli.*

By and large, however, Ichorin is preferably used to treat specific disease states when the Ichorin has been obtained from the serum of animals which have been specifically sensitized. Thus, the treatment of the following diseases with Ichorin derived from animals sensitized with the indicated sensitizing antigens may be achieved:

| Disease State | Sensitizing Antigen |
|---|---|
| Gonorrhea | *Neiserria gonorrhaeae* |
| Brucellosis | *Brucella suis* |
| | *Brucella abortus* |
| | *B. Meletensis* |
| Pseudomonas | *Pseudomonas aeruginosa* |
| Tetanus | *Clostridium tetani* toxoid |
| Miliary tuberculosis | Complete Freunds' adjuvant |
| Candidiasis | *Candida* |
| Cryptococcosis | *Cryptococcees neogormans* |
| Histoplasmosis | *Histoplasma capsulatum* |
| Amebiases | *Entameba histolytica* |
| Chagas' Disease | *Trypanosoma* |
| Leishmaniasis | *Leishmania* |
| Malaria | *Plasmodia* |
| Herpes | *Herpes virus type* (HSV-1) |
| | *Herpes virus type* (HSV-2) |
| Zoster | *Varicella-Zoster* |
| Cytomegalovirus mononucleosis | *Cytomegalovirus* |
| Hepatitis | |
| Pneumonitis | |
| Influenza | Multivalent influeza virus vaccine |
| Congenital Rubella | Rubella viral antigen |
| Chlamydial infections (psittacosis, lymphogranuloma venereum, trachoma-inclusion conjunctivitis | *Chlamydia trachomatis* |
| | *C. psittaci* |

Ichorin also has a high degree of usefulness in the veterinary field of medicine in the treatment of many disease states. Unfortunately, in many instances, such as when cattle are positive in their skin tests for tuberculosis, the animals are not used for human consumption. However, Ichorin is useful in treating distemper in dogs, shipping fever in cattle, infectious hepatitis and Mareks Disease in chickens.

Another use is to shorten the immunization lag period when Ichorin is used in conjunction with vaccines, such as for example the co-administration of tetanus toxoid.

The dose of Ichorin may be determined in a manner similar to the techniques known in the art and which have been developed for transfer factors. For example, the peripheral white blood cells of the incompetent patients are tested to determine the point of reaction to specific antigens (utilizing such tests as the lymphocyte transformation, the macrophage migration inhibition factor tests or the Rosette formation tests). With this point determined, the patient is treated and the blood is monitored to keep the level at that point wherein the white blood cells are reactive to the antigens.

In general, Ichorin may be administered orally or parenterally, at a dose range of 5–50 mgm to an animal weighing 1 to 100 kilograms. The duration of a single treatment is about 1 to 4 months.

Ichorin may be used alone or in conjunction with other known chemotherapeutic agents. Obviously, when so used, Ichorin may be formulated in accordance with the methods and substances are commonly used in the pharmaceutical art and include preparations such as injectables, tablets, capsules, drops, elixers, and the like. Preferably Ichorin will be orally administered.

We claim:
1. Ichorin.
2. Ichorin$_1$.
3. Ichorin$_2$.
4. A process for isolating Ichorin which comprises subjecting the blood sera of a disease state sensitized animal to electrophoretic separation from a Geon-Pevikon system utilizing an 0.05 ionic strength, pH 8.2 Veronal buffer with a constant current of 50 milliamps and about 300 volts for 18 hours at 6° C, isolating separated pools of gamma, beta and alpha globulins and albumins and subjecting the isolated gamma globulin pool to a second electrophoretic process utilizing a 0.025 ionic strength, pH 8.2 Veronal buffer with a constant current of 10-20 milliamps and about 400-450 volts, for about 18 hours and separating material from the 15th-32 cm sections from the cathode end of the block.

5. A process for preparing Ichorin which comprises sensitizing a warm-blooded animal with an antigen, bleeding said sensitized warm-blooded animal approximately 3 weeks thereafter, separating the serum from the whole blood and isolating Ichorin from the serum.

6. A process according to claim 5 wherein said warm-blooded animal was sensitized with a Candida antigen.

7. A process for treating specific disease states amenable to Ichorin therapy which comprises administering to an animal suffering there from a therapeutically advised amount of Ichorin derived from the blood serum of an animal previously sensitized with the sensitizing antigen for that disease state.

8. A process according to claim 7 wherein said specific disease state is Candidiasis.

9. A process according to claim 7 wherein said specific disease state is Gonorrhea.

10. A process according to claim 7 wherein said specific disease state is Brucellosis.

11. A process according to claim 7 wherein said specific disease state is Schigellosis.

12. A process according to claim 7 wherein said specific disease state is Pseudomonas.

13. A process according to claim 7 wherein said specific disease state is Tetanus.

14. A process according to claim 7 wherein said specific disease state is Miliary tuberculosis.

15. A process according to claim 7 wherein said specific disease state is Cryptococcosis.

16. A process according to claim 7 wherein said specific disease state is Histoplasmosis.

17. A process according to claim 7 wherein said specific disease state is Amebiases.

18. A process according to claim 7 wherein said specific disease state is Chagas' Disease.

19. A process according to claim 7 wherein said specific disease state is Leishmaniasis.

20. A process according to claim 7 wherein said specific disease state is Malaria.

21. A process according to claim 7 wherein said specific disease state is Herpes.

22. A process according to claim 7 wherein said specific disease state is Zoster.

23. A process according to claim 7 wherein said specific disease state is *Cytomegalovirus mononucleosis*.

24. A process according to claim 7 wherein said specific disease state is Influenza.

25. A process according to claim 7 wherein said specific disease state is Congenital Rubella.

26. A process according to claim 7 wherein said specific disease state is Chlamydial infections.

27. A process according to claim 7 wherein said specific disease state is distemper in dogs.

28. A process according to claim 7 wherein said specific disease state is shipping fever in cattle.

29. A process according to claim 7 wherein said specific disease state is infectious hepatitis.

30. A process according to claim 7 wherein said specific disease state is Mareks Disease in chickens.

* * * * *